United States Patent [19]
Bruce et al.

[11] 4,446,721
[45] May 8, 1984

[54] ATMOSPHERIC LIQUID WATER CONTENT MEASUREMENT AND CALIBRATION SYSTEM

[75] Inventors: Charles W. Bruce, Las Cruces, N. Mex.; Ralph J. Brewer, Zurich, Switzerland

[73] Assignee: The United States of America as represented by the Secretary of the Army, Washington, D.C.

[21] Appl. No.: 307,136

[22] Filed: Sep. 30, 1981

[51] Int. Cl.$^3$ .............................................. G01N 27/06
[52] U.S. Cl. ........................................................ 73/29
[58] Field of Search ................... 73/29, 73, 335, 336.5; 340/60 L

[56] References Cited

U.S. PATENT DOCUMENTS 2,702,471  2/1955  Vonnegut .............................. 73/29

OTHER PUBLICATIONS

Article, Applied Optics, vol. 19, No. 19, Oct. 1, 1980, "Experimentally Determined Relationship Between Extinction Coefficients and Liquid Water Content", by C. W. Bruce et al.

Primary Examiner—Stephen A. Kreitman
Attorney, Agent, or Firm—Robert P. Gibson; Jeremiah G. Murray; John W. Redman

[57] ABSTRACT

This system is a combination of two techniques which are used together effectively combining their features. One technique is an absolute measurement based on mass accumulation rate and used primarily for calibration purposes. The mass accumulation rate on a filter, when divided by the flow rate of the medium through this apparatus, yields the droplet density. The second technique is a differential measurement with two adjacent sampling inlets, one is unrestricted while the other is inertially filtered to eliminate water droplets. The two flow streams in the differential system are cyclically sampled and the combined flow passes a heated wire grid designed to evaporate droplets encountered. The resulting oscillating signal (with DC component) is fed into a lock-in amplifier whose output is the rms value of the difference signal. The vapor component is thereby nearly eliminated and the signal is processed by the phase-locked signal-to-reference detection technique which produces very high sensitivity.

6 Claims, 7 Drawing Figures

ATMOSPHERIC LIQUID WATER CONTENT MEASUREMENT AND CALIBRATION SYSTEM

The invention described herein may be manufactured, used, and licensed by or for the Government for governmental purposes without the payment of any royalties thereon.

BACKGROUND OF THE INVENTION

This invention relates to a technique for measurement of the liquid water content of clouds or fog, using a hot-wire sensor; and also calibration of the system.

The liquid water content of fogs and clouds is still one of the more fundamental variables that cloud physicists attempt to measure. Its distribution and evolution are relevant in cloud seeding, cloud modeling and cloud microphysics. Of the instruments currently available to measure liquid water, the John-Williams hot wire has been the most widely used. In this instrument a constant current passing through a wire exposed to the airstream heats the wire, and its temperature is monitored to give a measure of the liquid water. A similar wire which is kept dry is used to compensate for the heat supplied to the air moving past.

Merceret and Schricker, in the Vol. 14, April 1975 issue of the Journal of Applied Meteorology, pp. 319-326 describe a "nimbiometer" in which a hot wire is maintained at a constant temperature and the power monitored. Although this more readily permits analytic treatment, this instrument, like the Johnson-Williams, still requires either a wet wind tunnel or another liquid water instrument for calibration. Devices which yield the full droplet size distribution, such as the Knollenberg optical scattering probe or the older soot slides are also used to determine liquid water by integration of the droplet spectrum. The former is expensive, technically sophisticated, and requires computer backup to provide a real-time output of the liquid water, while the latter is labor-intensive in postflight analysis and also discriminates against the larger droplets because of its small sample volume.

King et al in an article in the December 1978 issue of the Journal of Applied Meteorology, pp. 1809-1813, describe "A Hot-Wire Liquid Water Device Having Fully Calculable Response Characteristics" that is robust, requires at most a simple dry calibration, has a stated sensitivity of 0.02 gram/cubic meter, a response time of the order of 0.05 seconds and an accuracy of about 5 percent at 1 gram/cubic meter (more dense than thick fog).

Determination of electro-optical (E-O) systems performance under low visibility conditions such as fogs and hazes is currently a problem whose solution is among the top priorities. A relationship is being sought between the propagation properties of the visible or infra-red radiation and meteorological parameter(s). For fog, this has been done in theory using liquid water content, i.e. mass density of the atmospheric water droplet content. This has caused very high level of interest relative to measurement systems for liquid water content. Meteorologists have stated that they have no satisfactory liquid water content (LWC) systems for ground based use.

SUMMARY OF THE INVENTION

An object of the invention is to provide a satisfactory system of liquid water measurement for primarily for stationary and possibly adaptable for aircraft borne measurements.

A feature of the invention relates to a single grid differential system. Summarized most simply, this system is a combination of two techniques which are used together, effectively combining their features. One technique is an absolute measurement based on mass accumulation rate and used primarily for calibration purposes. The mass accumulation rate on a filter, when divided by the flow rate of the medium through this apparatus, yields the total droplet mass density. The second technique is a differential measurement with two adjacent sampling inlets, one is unrestricted while the other is inertially filtered to eliminate water droplets. The two flow streams in the differential system are cyclically sampled and the combined flow passes a heated wire grid designed to evaporate droplets encountered. The resulting oscillating signal (with DC component) is fed into a lock-in amplifier whose output is the rms value of the difference signal. The vapor component is thereby subtracted and the signal is processed by the phase-locked signal-to-reference detection technique which produces very high sensitivity by virtue of minimizing the noise bandwidth.

A point which is very important in the motivation for this technique is that the vapor mass content in the atmosphere is generally much higher than that of the droplets. When hot wire cooling type measurements are used, even when one takes advantage of the 540 calories/gram heat of vaporization "gain" and for relatively heavy fogs, the cooling effect of the vapor exceeds that of the droplets and the effects of fluctuations and drift in the vapor component is effectively magnified with respect to the droplet signal.

To summarize;

(a) one single grid is used rather than two independent hot wires whose electrical characteristics generally drift yielding false signals. Since the single grid of this application is compared with itself, this drift is eliminated.

(b) the relatively large vapor contribution is then subtracted in the comparison of signals of the vapor and unfiltered throats. While there may be small differences between the throats, this has been found to be both small and, as expected, not significantly a function of the Liquid Water Content. It therefore simply forms an invariant baseline.

(c) this system uses a calibration scheme which is designed specifically for high accuracy. Absolute and relatively direct calibration of hot wire devices is not simple nor is it likely to be at all accurate.

(d) the Liquid Water Content signal from the signal grid device (whose frequency is that of the throat selection rate) appears as the RMS voltage output of a phase sensitive amplifier giving a much higher signal to noise ratio than with ordinary amplifiers. Effectively this means more sensitivity for the system.

(e) a system, then, based on the comparative throat, single grid device, detected with a phase sensitive amplifier and calibrated using an independent absolute techique should be accurate, stable and very sensitive.

DETAILED DESCRIPTION

Figure 1:
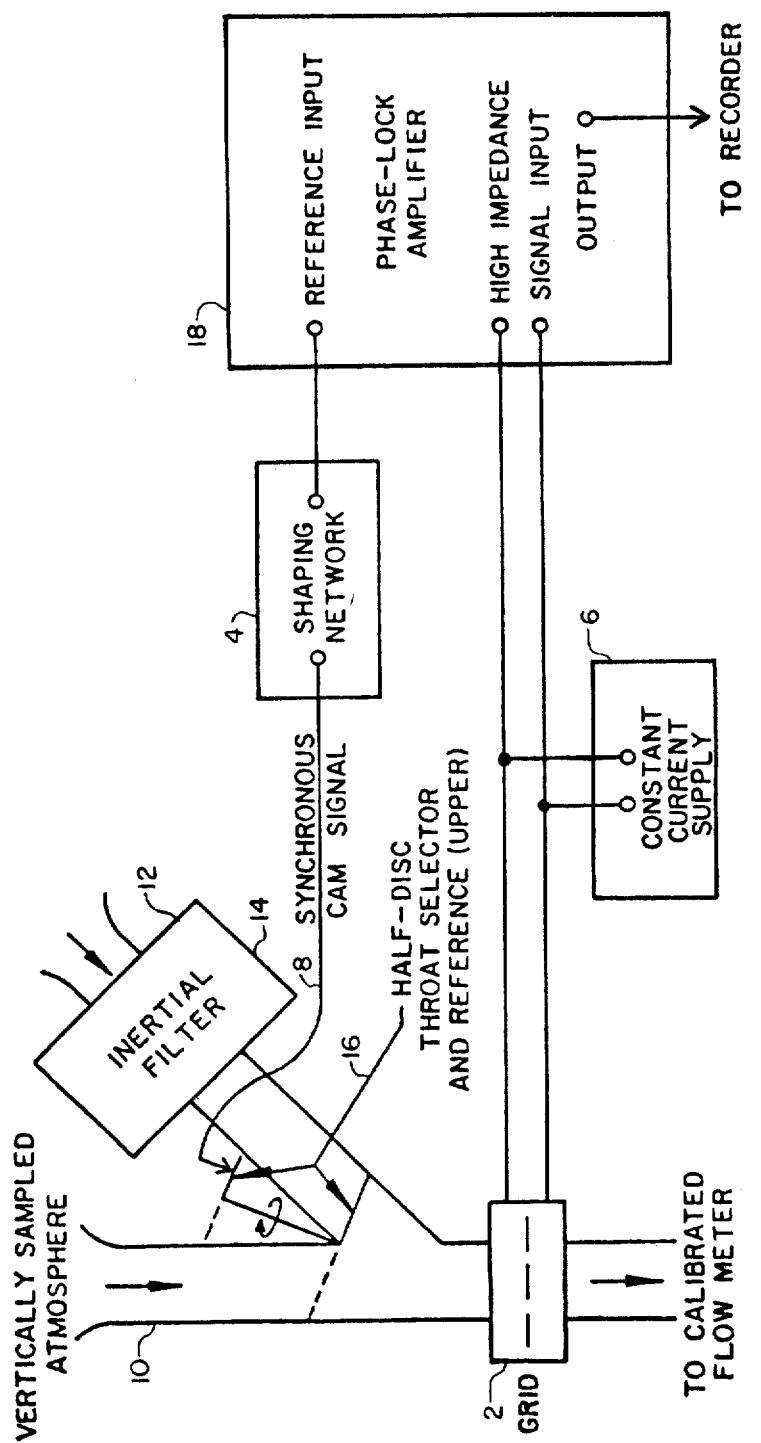
FIG. 1 is a schematic block diagram of the differential system.

A schematic for the differential system is shown in FIG. 1.

The water vapor/droplet inlet throat 10 is oriented vertically upward to minimize losses due to settling of large particles on measurement system components prior to their grid contact. The throat 12 through which the vapor enters contains an inertial filter 14 for the removal of droplets, i.e. a chamber with a tortuous course for the droplets and material to collect the impacting particles. Various configurations have been used to determine the most effective configuration for the inertial filter. The current (and much used) configuration of the invention involves the use of droplet capturing flannel sections adjacent to the air flow path. The signals from the two throats are successively and repeatedly sampled by a rotating half-disc throat selector 16 and reference (upper). The resulting flow passes the nichrome wire grid 20 which is woven orthogonally to the direction of flow on a ceramic core. Single and double layer grids have been used. A synchronizing signal on lead 22 from either the throat selection half-disc 16 or a similar but smaller secondary half-disc (on the same shaft) can be obtained for the phase lock amplifier reference input. This reference signal might involve either a microswitch or an LED with silicon light detector. This reference is then processed by a simple RC network 24 to more nearly resemble a sine wave for ease of detection by the phase-lock amplifier.

A power source 26 interactive with the grid impedance is used: a constant current power supply changes the voltage in proportion to that in resistance. The voltage applied to the grid (approximately 50 ohm) is also applied to the very high impedance phase-lock signal amplifier 30 (1 to 10 megohm) so that there is virtually no interaction with the latter unit. The measured voltage change is therefore proportional to the resistance change which, in turn, is approximately a linear function of the temperature change. If the impinging droplets are all completely evaporated by the high temperature wire, the temperature change will be approximately proportional to the impacting droplet mass (The wire diameter is selected to be much larger than the fog droplets). Of course one does not expect that all droplets will be completely evaporated (some will involve only partial encounters) but the implied proportionality between signal and total mass density has been upheld by the data. Both flow streams pass the same grid so that equalization and drift due to differences in geometry and physical characteristics are minimized. For throat selector operating frequencies less than 10 Hz, the phase-lock amplifier 30 may be an Ithaco model 393, brown card or red card. At higher operating frequencies most commercial phase-lock amplifiers will do. The power supply 26 may be a Hewlett-Packard 0–500 milliampere unit.

The mass accumulation technique requires relatively long integration times when droplet concentrations are low but is quite direct, straightforward for purposes of analysis and therefore appropriate for calibration of the differential system. The filter element consists of multiple layers of flannel material on a screen base. The important point here is that water would clog (and therefore pass) a two dimensional filter whereas the water droplets continue to collect and coalesce on the fibers of a three dimensional filter. Collection as a function of the number of layers of flannel has been determined for adequacy: it will vary for a different material.

Figure 7:
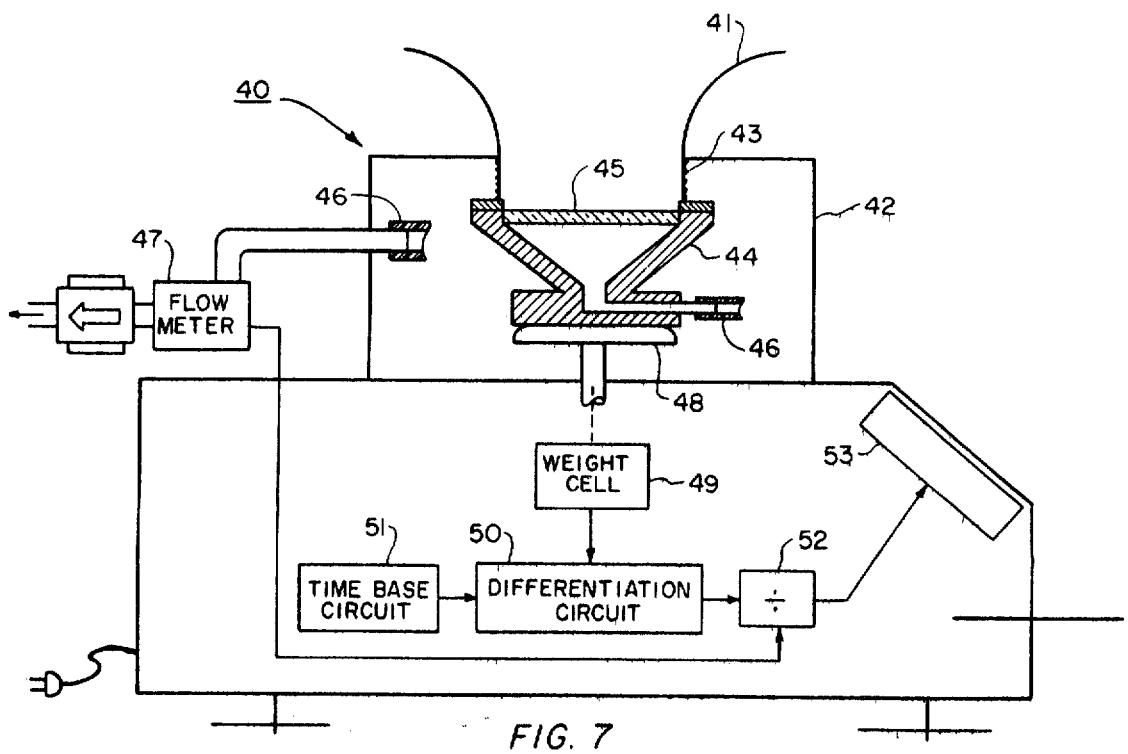
FIG. 7 is a schematic diagram of the major components of a real time calibration system.

Two calibrating filter techniques are used: one involves off-line analysis and the other is a nearly real time measurement. In the former case filter cells are inserted into the intake apparatus with o-ring seals and removed after the sampling period. They are then placed in a small airtight container in which they were pre-weighed. The post measurement weighing may be performed at any later time since the mass is now contained. This system works very well and integrating times from fifteen seconds to four minutes have yielded good reproducibility even for densities corresponding to light fogs and relatively low flow rates. It should be noted that we have found that the equilibrium weight of flannel is a (small) function of the ambient relative humidity. This factor is corrected for by having made measurements of mass accumulation as a function of accumulation time for various values of the relative humidity. The second (real time) calibrating filter approach shown in FIG. 7 uses a sampling unit 40 built into an electronic balance. The calibration unit 40 consists of fog intake bell 41 connected to housing 42 by bell adjusting threads 43. The height of bell 41 is maintained in operation to be close to but not touch intake cone 44. Fog laden-air is drawn through flowmeter 47, flexible thin-wall rubber tubing 36, intake cone 44, and felt grid assembly 45 where droplets and moisture are trapped for weighing. Any increase in weight pushes balance top plate 48 down which is converted to an electrical signal by electronic balance weight cell 49. This output is differentiated in circuit 50 with respect to time from circuit 51. This differentiated signal is further divided, in circuit 52 by the output of flowmeter 47. This final signal is provided to digital readout 53 for a continuous output.

In environmental chamber equilibrium measurements the small filter cells and off line analysis have been very useful, but the real time measurement might be suitable for field applications which do not exceed several hours of unattended use. the applicability of the differential system appears to be more general, i.e. high sensitivity and real time measurements for extended periods, if the inertial filter incorporates a drain for the collected droplets. This can be done by orienting the multi-stage filter inlet throat vertically downward so that each successive stage is above the previous one in the gravitational field. If each stage consists of layers of flannel stretched across a metal spacer with small open portion staggered between stages, the accumulated droplets will then move downward through the flannel and out. Effects on the water droplet signals due to variations in the tube radius, length and intake geometry have been studied for design purposes. The removeable grid is laced through holes in opposite sides of a ring machined from a ceramic like material called Boron-Nitride which does not char at high temperatures. This ring is inserted in a copper cylinder which helps to stabilize the temperature in the flow region around the grid. The temperature of the incoming moisture laden air is also stabilized by the high thermal conductivity metal of the mechanical system itself. Care is taken to maintain conditions for laminar flow within the system with the exception of the region of the throat-selector between the two channels. The differential sensor is mounted on an optical table for measurements within an environmental chamber.

Figure 2:
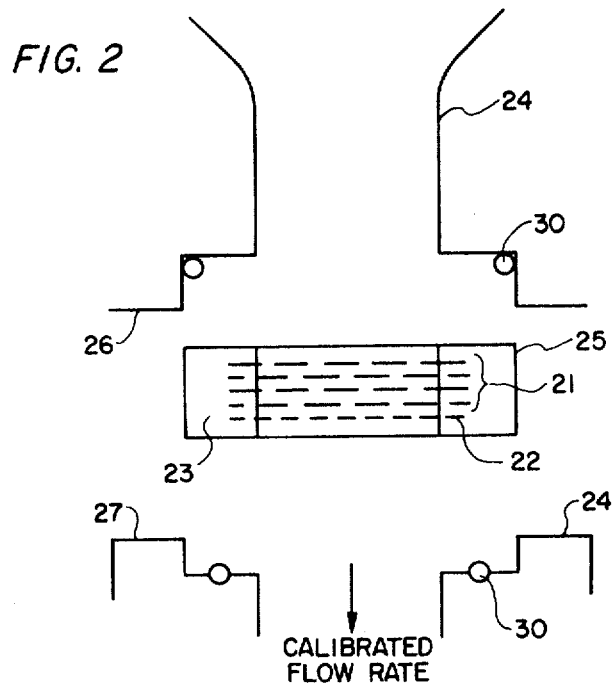
FIG. 2 is a schematic diagram showing a small calibrating filter unit.

A calibration or absolute sensor is mounted on a bracket adjacent to the differential unit for the chamber measurements. The base block incorporates O-ring seals under the filter unit and between the filter and the input tube. A sketch showing small and exploded calibrating filter unit is shown in FIG. 2. The flannel filter material 21 is held by a screw-in ring 23 on the upper side and is supported by a fine wire mesh 22 on the underside. Sampling filter module 25 fits in filter module seat 25 and faces 26 and 27 made congruent. O-rings 30 form a tight goal. The calibration process should result in a relationship between the differential signal and the mass density of the atmospheric water droplet content which relationship is effectively independent of the droplet size distribution within the bounds of natural occurrence for fogs. In order to characterize the behavior of the system several parametric studies were undertaken for the first prototype system which have bearing on this question and on operational properties. The rms signal voltage should, for a given flow rate, first increase with increasing grid current applied, since the temperature difference between medium and wire is also increasing. When the increasing wire temperature causes evaporation of the water droplets, the dependence of the signal on the current should decrease with further increase in the grid current. This condition of minimal signal increase with current should hold for measurements on fogs with particle distributions and densities representing the most dense expected. The set of measurements of FIG. 3 was performed for a size distribution which included significant mass contributions from relatively large particles (radii of 15 to 20 micrometer) and dense fog (greater than 1 gram per cubic meter). Fog densities of 1 gram per cubic meter are considered near realistic limits. A quantitative comment on this data is that for quite low flow rates, the signal voltages showed significant time fluctuations, presumably due to the passage of large droplets at a low rate; however, low density fog at the higher flow rates yielded quite steady signals by comparison.

Figure 3:
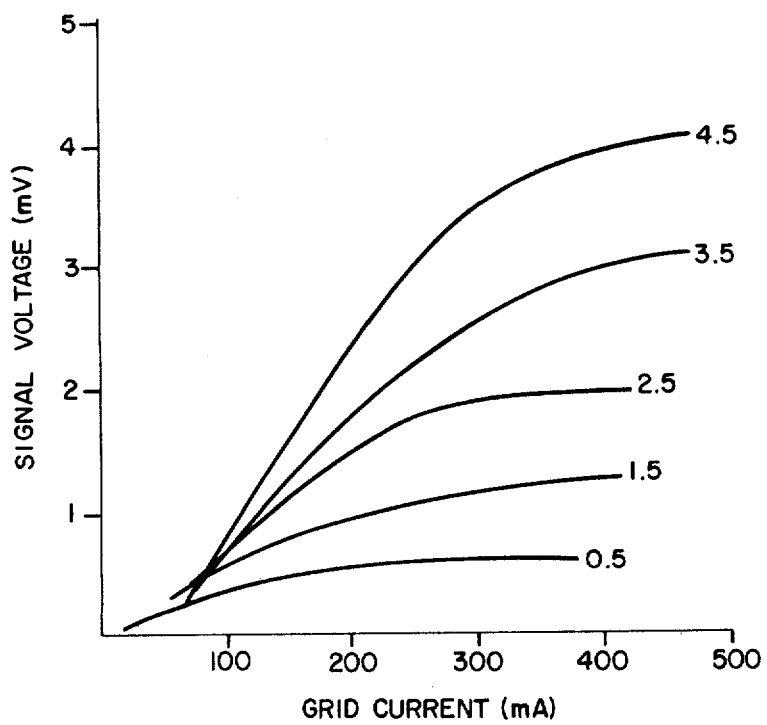
FIGS. 3–6 are graphs relating to performance of the system.
Figure 4:
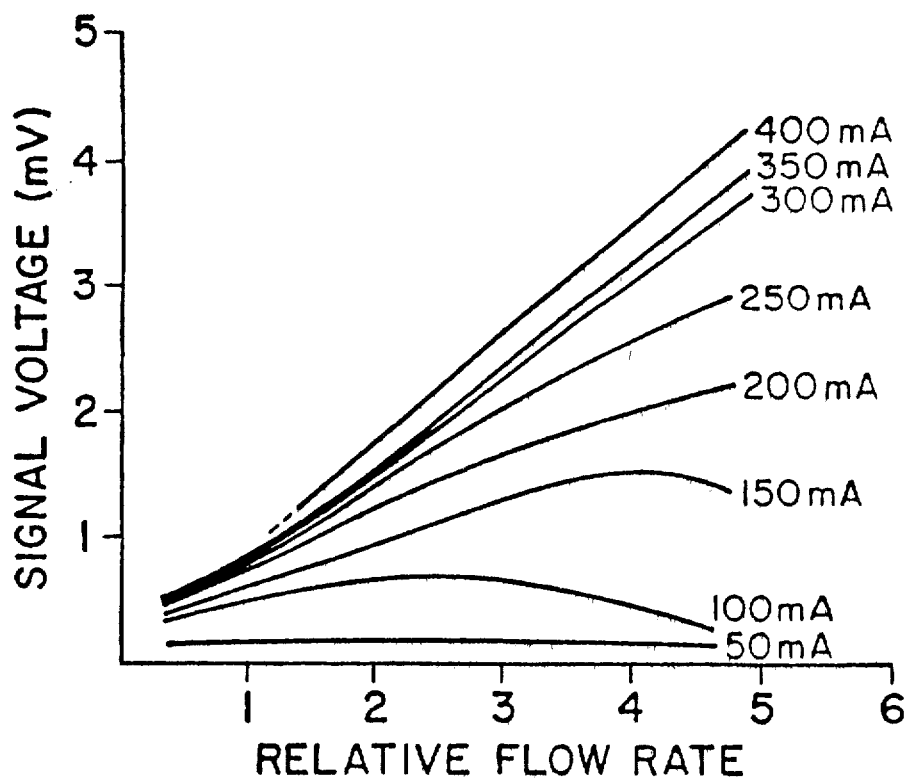

If the data of FIG. 3 are replotted for fixed currents, the relationship between signal and flow rate may be seen. This should be linear within, e.g. the evaporative current region. An example of this is shown in FIG. 4.

Figure 5:
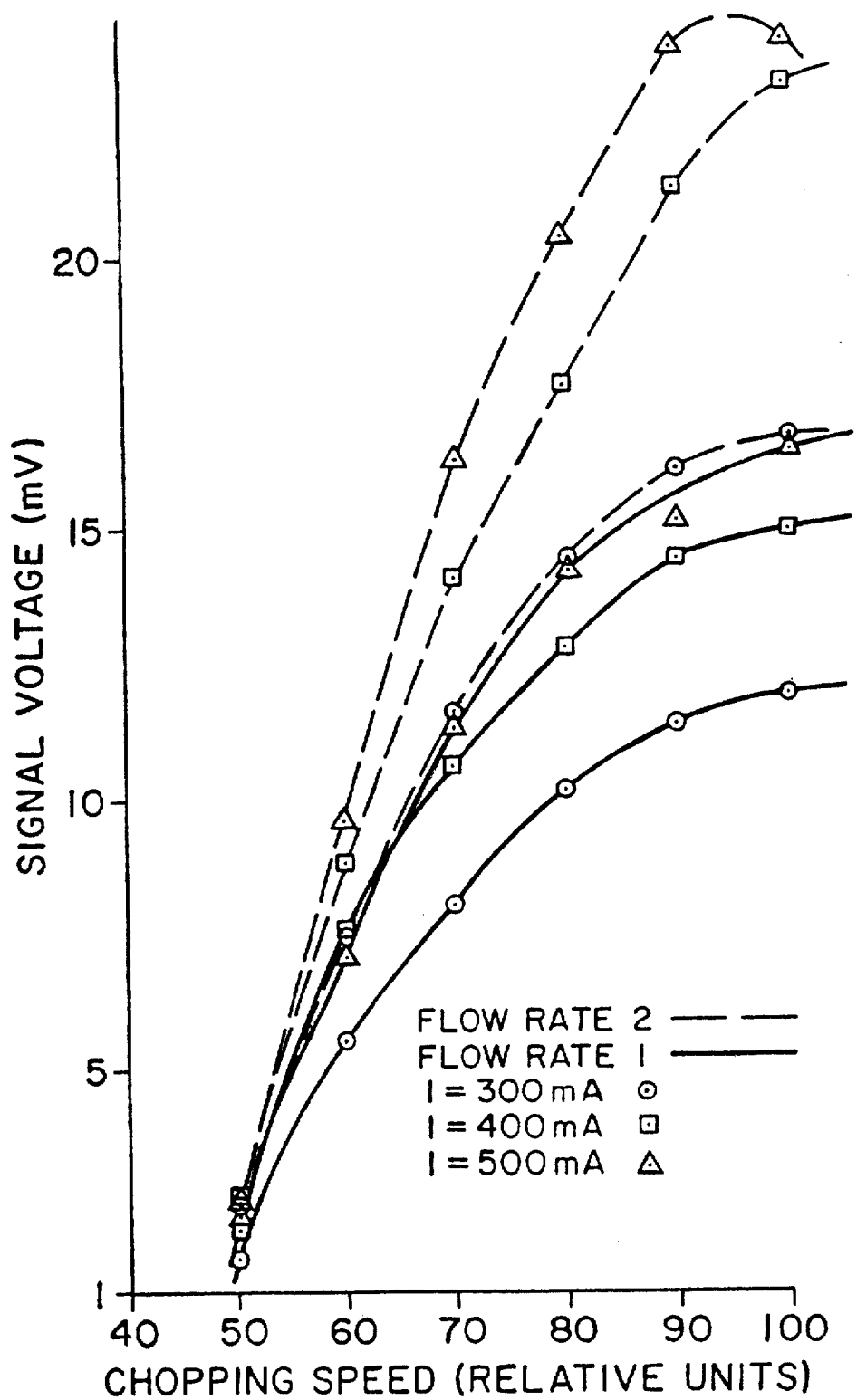

Another relevant measurement relates to the throat selection "chopping" rate. The conditions of the system relating the signal voltage to this rate are aerodynamic mixing of the contents of the two throats along the flow axis and orthogonal to it (uniformity in the plane of the grid) and response of the lock-in amplifier system as a function of the relatively low chopping frequency. Mixing effects are related in turn to the flow rate. FIG. 5 is a plot indicating the variation in efficiency for a given flow rate. When the flow rate is increased beyond the plot given, the signal may be expected to decrease again since the separation of the total and vapor content regions will become thinner along the flow axis and finally indistinct.

Figure 6:
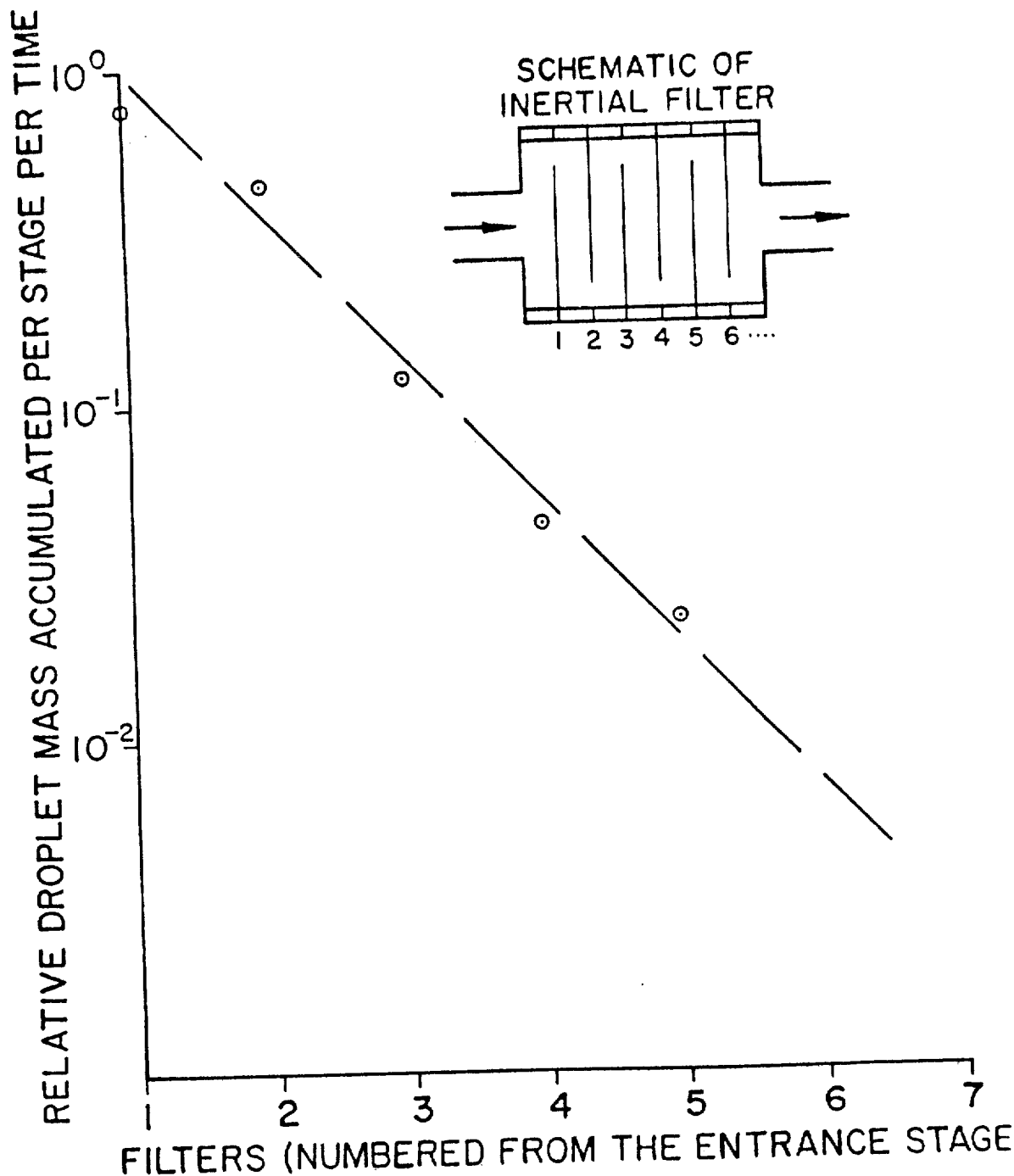

Efficiency of mass collection on the inertial filter was also a project study. It might be noted here that for water droplets drawn from the atmosphere through three layers of flannel filters were sufficient though tests were continued through nine layers. However, in the inertial filter, the droplets pass levels of filters with staggered open passages. This surface collection technique also collects the droplets for fog when a sufficient number of levels is used. The results of some measurements of this latter type are given in FIG. 6. Here the losses are normalized to that of the first stage. The exponential fit permits the calculation of the fractional mass lost. From the data shown, the loss is approximately two percent for a five stage filter.

Grids used have included single and double layers with no significant relative advantages.

Finally, the absolute measurement may be used to calibrate the relative measurement system. Actually the two systems are generally operated together; one providing high sensitivity and real time results and the other a continuing reference.

These may be considered either as separate or as supporting measurements. Both were designed to span low density to high density fogs, i.e. from less than $10^{-2}$ to greater than one gram from ground based applications. The relative system yields a time resolution of about two seconds. The time resolution of the absolute sensor depends on the density of the fog (for a given collection area and flow rate). The sensitivity of the current differential system first prototype is about $10^{-3}$ grams per cubic meter for an accuracy of about 20%. Accuracy improves to an estimated 5% or better for valves greater than $5 \times 10^{-3}$ grs/m$^3$.

A set of measurements involving all three types of sensors has been packaged for field applications and used at Meppen, Germany (Nov–Dec, 1980). The offline filter unit was gimbel mounted into the wind to minimize large particle losses and the real time unit was shuttered to obtain periodic (rather than continuous) measurements when winds were strong.

We claim:

1. Apparatus for measurement of atmospheric liquid water content comprising intake apparatus having a first throat means for sampling a flow of ambient atmosphere, and a second throat means for sampling flow of a filtered atmosphere and an inertial filter means for filtering said atmosphere by removing droplets of water;

selection means for cyclically and alternately sampling the inputs from said first and second throats;
   a wire grid heater over which said flow from said selection means passes;
   a phase lock amplifier;
   electrical synchronizing means coupled to said selection means to supply a reference signal to said phase lock amplifier;
   a constant current source connected to said wire grid and also in parallel to a high impedance input of said phase lock amplifier, such that said wire grid is heated to evaporate water droplets encountered and a voltage across the grid proportional to its resistance is applied as an input signal to the phase lock amplifier, and said phase lock amplifier operating to supply an output which is the rms value of the difference signal between the half cycles of said reference signal, whereby the wafer vapor component as opposed to the water droplet component of sampled ambient atmosphere is eliminated to thereby measure the liquid water content.

2. Apparatus as set forth in claim 1, wherein said selection means includes a rotating half-disc throat selector.

3. Apparatus as set forth in claim 2, wherein said synchronizing means includes a resistance-capacitance shaping network operatively between said selection means and said phase lock amplifier to make the signal more nearly a sine wave.

4. Apparatus as in claim 1 further comprising calibration means comprising water droplet accumulating filter means,
   intake apparatus means for receiving said filter,
   time indicating means for providing time base lengths of accumulation of water by said filter means; and
   differential weight indicating means for providing an output indicative of water weight alone.

5. Apparatus as set forth in claim 4 wherein said differential weight indicating means is integral with said means for receiving said filter.

6. Apparatus as in claim 5 wherein said output is electrically differentiated with respect to time and divided by flow rate to provide a continuous read-out.

* * * * *